(12) United States Patent
Mittal et al.

(10) Patent No.: US 8,147,429 B2
(45) Date of Patent: Apr. 3, 2012

(54) PELVIC FLOOR FUNCTION DIAGNOSTIC AND THERAPEUTIC STATION AND USES THEREOF

(75) Inventors: Ravinder K. Mittal, La Jolla, CA (US);
Jianmin Liu, Chesterfield, VA (US);
Charles W. Nager, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1556 days.

(21) Appl. No.: 11/348,183

(22) Filed: Feb. 6, 2006

(65) Prior Publication Data

US 2007/0185417 A1    Aug. 9, 2007

(51) Int. Cl.
*A61B 5/103* (2006.01)
*A61B 5/117* (2006.01)

(52) U.S. Cl. ..................................... 600/591

(58) Field of Classification Search .............. 600/587, 600/588, 591, 38
See application file for complete search history.

(56) References Cited

U.S. PATENT DOCUMENTS

| | | | |
|---|---|---|---|
| 6,174,290 B1 * | 1/2001 | Cho | 600/551 |
| 7,330,762 B2 | 2/2008 | Boveja et al. | 607/39 |
| 2004/0122341 A1 * | 6/2004 | Walsh et al. | 600/591 |

FOREIGN PATENT DOCUMENTS

WO    WO00/09013    *    2/2000

* cited by examiner

*Primary Examiner* — Max Hindenburg
*Assistant Examiner* — Jonathan M Foreman
(74) *Attorney, Agent, or Firm* — Benjamin Aaron Adler

(57) ABSTRACT

The instant invention provides a pelvic floor function diagnostic and therapeutic station, which includes a vaginal/anorectal plug and station. The important components of the station are a catheter holder with a pressure measuring (sleeve sensor or other alterative) to measure the constrictor function of the pelvic floor muscle, a vertical force transducer system to measure the elevator function of the pelvic floor muscle and a modular support table or a chair to hold the subject position. The diagnostic and therapeutic station thus allows for simultaneous measurement of the constrictor and elevator functions of the pelvic diaphragm. The station can also be used to treat impaired pelvic floor function via biofeedback therapy.

21 Claims, 6 Drawing Sheets

PELVIC FLOOR FUNCTION DIAGNOSTIC AND THERAPEUTIC STATION AND USES THEREOF

BACKGROUND OF THE INVENTION

1. Field of the Invention

The present invention relates generally to the field of diagnosis and therapy of pelvic floor muscle disorders. More specifically, the present invention relates to pelvic floor function diagnostic and therapeutic station that can be used for diagnosis and treatment of pelvic floor muscle disorders.

2. Description of the Related Art

The pelvic floor muscles (PFM) form the floor of the pelvic basin and performs two major functions, an elevator function for pelvic organs and constrictor function for three orifices, urethra, vagina and anal canal. The elevator function of the pelvic floor supports the pelvic viscera and is probably important for the prevention of rectal, vaginal and bladder prolapse. Constrictor function, on the other hand is involved in the closure mechanism of urethra, vagina and anal canal. In individuals with normal pelvic muscle function, the pelvic floor muscle contracts simultaneously and this contraction precedes the increase in abdominal pressure as an unconscious automatic co-contraction (1,2). This contraction can be described as a cranial movement of the pelvic floor and closure around the urethra, vagina and anal canal. Pelvic floor muscle weakness can thus cause prolapse of pelvic organs and incontinence of urine, feces and poor vaginal closure. Therefore physical therapists often target the pelvic floor muscle for management of urinary and fecal incontinence, and other pelvic-floor disorders.

Measuring pelvic floor muscle strength is important not only in the diagnosis of impaired pelvic floor muscle function but also to evaluate the recovery of pelvic floor muscle function after therapeutic intervention. There are several devices that can measure pelvic floor muscle strength, they include, vaginal devices to measure the electromyographic signals of pelvic floor muscles, perineal dynamometer, various types of balloons, strain gauge and force transducers to measure vaginal closure strength. However none of these devices measure constrictor and elevator functions of pelvic floor muscles precisely. Furthermore, these devices cannot measure the length tension curve of the constrictor and elevator function of the pelvic floor muscle. It is important to measure the length tension relationship of pelvic floor muscles because this relationship is an important indicator of the actual strength of these muscles. Furthermore, to treat pelvic floor muscle weakness, it is often necessary to train pelvic floor muscles via biofeedback therapy.

There are two major problems with vaginal pressure measurements. First, air filled balloons and water filled balloons, used by most of the investigators, do not measure absolute pressures. Through the work of several investigators it became clear in 1970's that infusion manometry is a better technique to measure absolute pressure in sphincters, esophagus and other parts of GI tract. Secondly, vagina is approximately 10 cm long; a portion of it lies above pelvic diaphragm and a portion in the hiatus of pelvic diaphragm. None of the techniques used in the published literature made any attempt to distinguish pressures in different portions of the vaginal canal. It is likely that the segment of vagina located above pelvic diaphragm will reflect intra-abdominal pressure and the segment located in pelvic diaphragm hiatus will actually measure squeeze pressure from pelvic diaphragm muscle. Pneumatic resistance chamber used by Kegel was 8 cm long (3) and probably spanned across the entire length of vaginal canal and measured average pressure, rather than true pelvic floor muscle squeeze pressure. Techniques used by other investigators also did not make any attempt to distinguishing pressures from different segments of vaginal canal.

U.S. Pat. No. 6,862,480 discloses a device for training pelvic floor muscles in order to prevent or treat urinary or fecal incontinence. The device comprises a probe having a pressure sensor and a vibrator and a microprocessor connected to the sensor and the vibrator. This device however does not measure the constrictor and elevator function of the pelvic floor muscles. U.S. Pat. Nos. 6,862,480, 6,773,380, 6,562,018 and 6,068,581 describe different devices either for testing or exercising pelvic floor muscles. However none of these devices can measure a both constrictor and elevator function of the pelvic floor muscles and furthermore they do not use the values obtained therein to provide biofeedback therapy to these muscles.

U.S. Pat. No. 6,468,232 describes a device to measure pelvic floor muscle properties using two or more elongated blades disposed adjacent to each other and one or more sensors that can sense the deflection of one blade with respect to another when the blades are subjected to an external force. However the pelvic floor muscles pressure measured by this apparatus includes abdominal pressure and requires a complicated method to arrive at actual pelvic floor muscle forces. Furthermore, this device does not measure the elevator function of the pelvic floor muscles. This device also does not provide a means to offer resistance to pelvic floor muscles in order to exercise these muscles against resistance.

Thus, the prior art lacks a device that can, (1) measure the constrictor and elevator function of the pelvic diaphragm simultaneously; (2) measure the length tension curves of the constrictor and elevator functions of pelvic floor muscle; and (3) interpret such measurements to provide biofeedback therapy if a subject is in need of such therapy. The instant invention fulfills this need in the art.

SUMMARY OF THE INVENTION

The present invention provides a vaginal/ano-rectal plug and a station, which together forms the pelvic floor function diagnostic and therapeutic station (PFFDTS). The important components of this diagnostic and therapeutic station are: (a) a means to measure the constrictor function of pelvic floor muscle and its length tension characteristics; (b) a means to measure the elevator function of pelvic floor muscle and its length tension characteristics; and (c) a modular support table or a chair to hold the subject in appropriate position.

In one embodiment of the present invention, the vaginal/ano-rectal plug comprises a catheter holder. There are several important aspects of this plug or catheter holder: 1) the anterior-posterior length of the plug is adjustable through a remotely controlled mechanical system, which enables changing the length of the puborectalis muscle; 2) the holder contains a manometer and sleeve sensor to measure the pressure exerted by the pelvic floor muscles.

In another embodiment there is a ball at one end of the holder and the other end of the holder is connected to a vertical force transducer. The force transducer can exert different vertical force on the holder and ball. The Force transducer sensor records cranio-caudal movement of the anal or vaginal canal against different resistances.

In yet another embodiment there are three surface electrodes on the catheter holder. The surface electrodes can measure the electromyographic (EMG) activity of the pelvic floor muscle and these electrodes may also be used for electrical stimulation of the pelvic floor muscles for a therapeutic effect.

In another embodiment, the signals recorded by different sensors are passed via an anchoring device on the support or chair to a computer and software system to record various physiological signals. In a related embodiment these measurements are used to provide biofeedback therapy using different exercises to a subject in need of such therapy.

In yet another embodiment, there is provided a pelvic floor function diagnostic and therapeutic station comprising: a) a catheter holder with a sleeve sensor or an equivalent pressure measurement system to measure the constrictor function of pelvic floor muscles; (b) a vertical force transducer system to measure the elevator function of the pelvic floor muscles; (c) a modular support table or a chair to hold the subject in appropriate position; and (d) a computer and software system to receive and process the measurements from (a) and (b). The instant invention also discloses a method to measure the constrictor and elevator function of the pelvic floor function using this station.

In another embodiment, there is provided a method to diagnose pelvic floor muscle dysfunction in a subject using the vaginal/ano-rectal plug and station of the instant invention. The method comprises: (a) measuring the constrictor function of pelvic floor muscles; and (b) measuring the elevator function of the pelvic floor muscles such that a change in measurements as compared to that observed in a normal subject is indicative that the subject suffers from dysfunction of the pelvic floor muscle.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments there of which are illustrated in the appended drawings. These drawings form a part of the specification. It is to be noted, however, that the appended drawings illustrate embodiments of the invention and therefore are not to be considered limiting in their scope.

DETAILED DESCRIPTION OF THE INVENTION

Figure 1A:
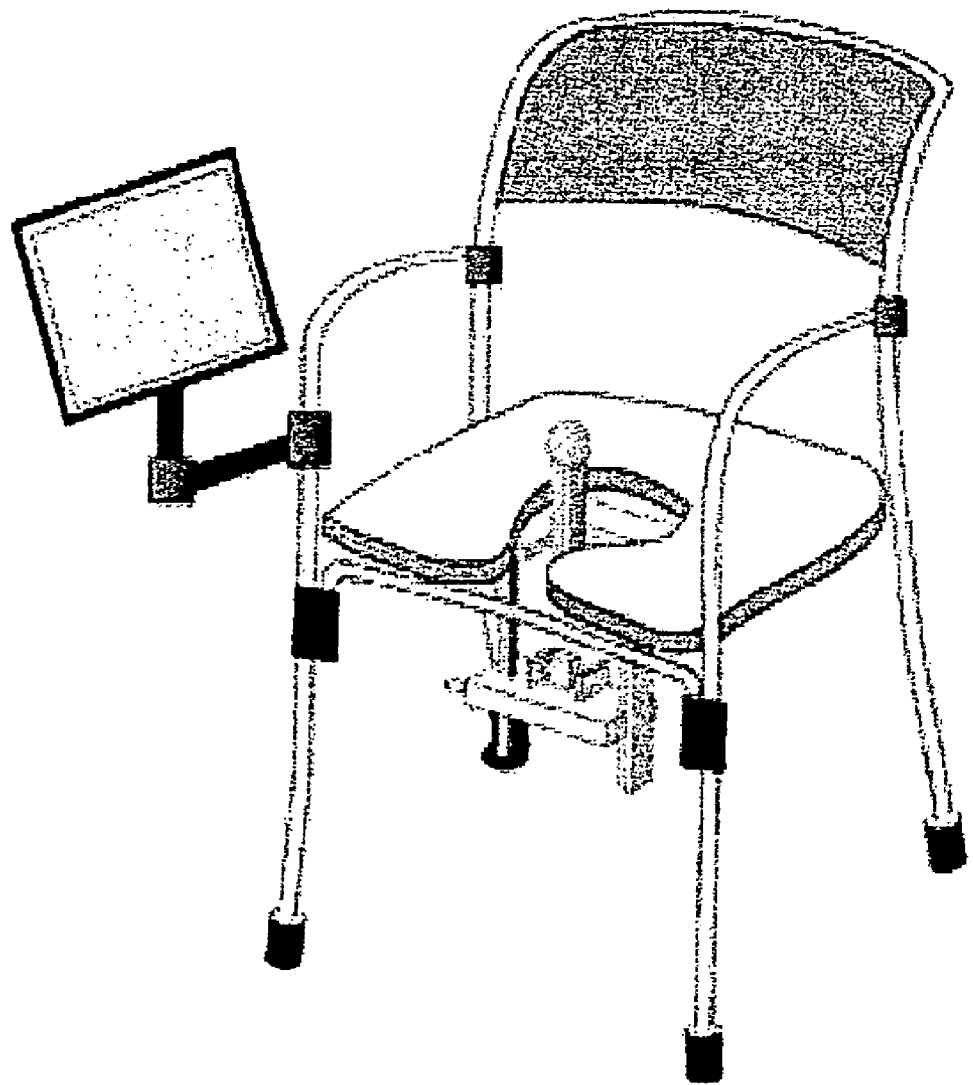
FIG. 1A is a model of the pelvic floor function diagnostic and therapeutic station.

Urinary incontinence, fecal incontinence, vaginal closure mechanism (sexual dysfunction) and urogenital prolapse are extremely common in women. One of the difficulties in assessing the precise role of pelvic floor muscle in the pathogenesis of these disorders is the lack of ability to quantitate pelvic floor muscle function. Clinical examination, physiologic measurements (vaginal pressure and electromyographic recordings) and imaging studies (X ray barium defecography, 3D ultrasound imaging and magnetic resonance imaging) have been used to measure pelvic floor muscle function but there is no consensus on the reliability and reproducibility of these measurements.

The pelvic floor muscle has two important functions: (1) to provide physical support to pelvic viscera (elevator function); and (2) to provide a constriction (sphincter function) action for the three orifices i.e., the anal canal, the urethra and the vagina, which traverse through the pelvic floor hiatus. The instant invention in one embodiment provides a vaginal/ano-rectal plug and station to simultaneously measure both the constrictor and elevator functions of the pelvic floor muscle. The vaginal/ano-rectal plug and station may also be referred to as a pelvic floor function diagnostic and therapeutic station.

It is contemplated that pelvic muscle weakness or dysfunction arises due to a lack of an ability to generate adequate force at rest and lack of an ability to generate adequate force with increase in its length for constrictor and elevator functions. The instant vaginal/ano-rectal plug and station is designed to measure constrictor and elevator functions at different muscle lengths to generate a length tension profile. Accordingly in another embodiment, the instant invention can be used to diagnose pelvic muscle dysfunction in a subject. A decrease in the constrictor and elevator functions in the patient as compared to values in a normal subject is indicative of pelvic muscle dysfunction in the patient.

In a related embodiment, the measure of constrictor and elevator functions can be processed in a computer using appropriate software for biofeedback therapy in a subject using different exercises. Examples of such exercises are contraction of pelvic floor muscles against resistance (resistance can be adjusted in the plug for both constrictor and elevator function) and during electrical stimulation of pelvic floor muscle. Such electrodes can be present on the instant plug to provide electrical stimulation to the pelvic floor muscles.

The following terms are described herein to clarify the subject matter disclosed in the instant specification:

Biofeedback therapy refers to a training technique in which a person learns how to consciously control involuntary responses such as muscle contraction. The person generally receives a visual, auditory or tactile signal that indicates how well the individual's muscles are responding to the commands of the individual's nervous system. For example if a subject suffers from pelvic floor muscle weakness, then the measure of pressure exerted by the individual's pelvic floor muscle is made available to the subject by a visual display such as a computer monitor. After examining these values, the subject can perform exercises to improve the pressure exerted by the subject's pelvic floor muscle by looking at the change in the pressure measurements in the visual display.

The puborectalis muscle is a large U-shaped skeletal muscle that wraps around the upper anal canal at the anorectal junction above the external anal sphincter and loops anteriorly to attach to the pubic bone.

The pelvic diaphragm consists of puborectalis muscle, right and left pubococcygeous muscles, and right and left iliococcygeous. Posteriorly, the coccygeous muscle joins these other muscle to complete the pelvic floor. Ischial tuberosities are the two bony points at the base of the pelvis.

The vaginal/ano-rectal plug sensor and station (pelvic floor function diagnostic and therapeutic station) of the instant invention comprises: (a) a means to measure the constrictor function of pelvic floor muscle; (b) a means to measure the elevator function of pelvic floor muscle; and (c) a modular support table or a chair to hold the subject position.

In another embodiment the station of the instant invention comprises a chair with an anchoring device to which the outer end of the plug is connected. The anchoring device enables connection of the plug to a computer and software system for making measurements based on the signals detected by the plug. Such measurements are then processed by the software system to provide biofeedback therapy to a subject in need of such therapy.

In another embodiment, the vaginal/ano-rectal plug comprises a catheter holder. The catheter holder has a pressure measuring unit such as a manometer and a sleeve sensor (water perfused or solid state transducer) to measure the rest and squeeze pressure of the vaginal canal. To ensure accuracy in measurements, a reverse perfuse sleeve sensor is preferable in the instant invention.

The catheter holder is preferably 80 mm in length. The diameter of the catheter holder may be varied using a mechanical device. More specifically this width varies between 10-40 mm. The mechanical device for varying holder diameter may comprise a holder adjusting level, holder adjusting shaft and a holder adjusting knob. Another possible mechanism to adjust the plug diameter is using an expandable plug and hydrostatic pressure. The variable width of the catheter holder (plug) enables increasing and decreasing the length of the puborectalis muscle and hence the pressure exerted by this muscle at different lengths can be estimated using the instant catheter holder. catheter holder may consist of two prongs with a mechanism to provide variable resistance between the two prongs which will allow a subject to perform constrictor function against different resistances to exercise pelvic floor muscles.

The puborectalis muscle is hypothesized to be a major source of vaginal pressure. This hypothesis is based on the premise that to generate squeeze pressure in the vagina, which is in the form of a cylindrical tube, usually a circular muscle arrangement is required. It is probable that the shortening of the puborectalis muscle pulls the anal canal, the vagina and the urethra in an anterior direction, thereby compressing these three structures against each other and in turn against the posterior surface of the pubic bone. This argument is supported by the observation that vaginal high pressure zone is circumferentially asymmetric with higher pressures oriented in the anterior and posterior directions. Thus it is reasonable to assume that the puborectalis muscle component of the pelvic floor muscle provides constrictor function of the pelvic diaphragm and vaginal manometry measures this function.

In another embodiment there are surface electrodes on the catheter holder, which may function to either measure the EMG activity of the pelvic floor muscle or to provide therapeutic electrical stimulation to these muscles when a subject is in need of such therapy. Preferably, the instant catheter holder has three surface electrodes. The electrodes may be made of platinum or any other conductive material known in the related art.

In another embodiment, at one end of the catheter holder is a ball. The ball is preferably 15-20 mm in diameter. The ball and catheter holder are connected to a force transducer via a force transducer rod. The force transducer, which may be placed in a transducer holder, exerts varying vertical force on the catheter holder and ball. This varying force in turn increases or decreases the resistance against which the pelvic floor muscle may contract. This arrangement enables measurement of the length tension relationship for that part of the pelvic floor muscle that is responsible for the cranio-caudal movements. Preferably the total length of the catheter holder and ball is about 80-100 mm. A strain gauge sensor or any other sensor that can measure vertical force is located on either the ball or the base of the catheter holder to measure the vertical force exerted by the pelvic floor muscles at varying length. A subject can perform elevator function against varying force applied by the transducer to exercise pelvic floor muscles.

It is contemplated that the pubococcygeus and ileococcygeus muscles of the pelvic floor provide the elevator function of the pelvic diaphragm and measurements of the cranio-caudal movement of the anal canal and vagina is a relatively non-invasive technique to measure the elevator function of the pelvic floor muscle. The pelvic floor convexity (towards the cranial end) increases with voluntary contraction, which lifts the pelvic floor resulting in cranial movement of anal canal, vagina and urethra. So a measure of this cranial movement during muscle contraction can be used as a reasonable metric to evaluate the elevator function of the pelvic floor muscle.

The catheter holder and the force transducer, which together comprise the force/pressure module is placed on a support. The support may be in the form of a chair to seat the subject who is to be evaluated for pelvic floor function or who is in need of therapy to correct pelvic floor muscle weakness. Modular support table allows subjects to sit on ischial tuberosities thus anchoring the subject's position in relationship to the vertical force transducer. The support may comprise a position adjusting level and a position adjusting knob to position the subject in the appropriate position for diagnosis or therapy using the instant invention. The support may further comprise an anchoring device, which receives a signal output from the different sensors on the catheter holder and the ball on the catheter holder. The signal from the anchoring device in turn is directed to a computer and software system for making measurements. These measurements relate to the length tension relationship for both the constrictor and elevator function of the pelvic floor muscle. A subject may also perform constrictor and elevator function against the variable force that can be applied on the pelvic floor muscles with the instant device for strengthening of the pelvic floor muscles. The computer screen mounted on the chair or the modular platform provides visual feedback of the pressure signal generated by the constrictor function and the isometric force generated by the elevator function.

In still another embodiment of the present invention, there is provided a pelvic floor function diagnostic and therapeutic station comprising: a) a catheter holder with a sleeve sensor or an equivalent pressure measurement system to measure the constrictor function of pelvic floor muscles; (b) a vertical force transducer system to measure the elevator function of said pelvic floor muscles; (c) a modular support table or a chair to hold the subject position; and (d) a computer and software system to receive and process said measurements from (a) and (b).

In another embodiment a method to measure the constrictor and elevator function of pelvic floor muscles using the station described supra is disclosed. The method comprises: (a) seating said subject on a chair, wherein the subject is resting on both ischial tuberosities; (b) positioning the catheter holder inside the rectum above the anal high pressure zone or in the vagina high pressure zone; (c) measuring the constrictor function at rest and squeeze pressure of the rectal or vaginal canal, wherein the diameter of the catheter holder is varied; and (d) measuring the elevator function of the pelvic floor muscles, wherein the resistance against which the muscles contract is varied via the force transducer.

The instant device can be used to quantify the active contractile and passive tissue properties of the pelvic floor muscles such as pelvic floor muscles strength, muscle endurance and fatigue. The contractile force resulting from electrical stimulation intra vaginally or intra rectally in women and intra rectally in man can also be measured using the instant device. The method and device can also be used to assess strengthening of pelvic floor muscles following therapeutic intervention.

Figure 1B:
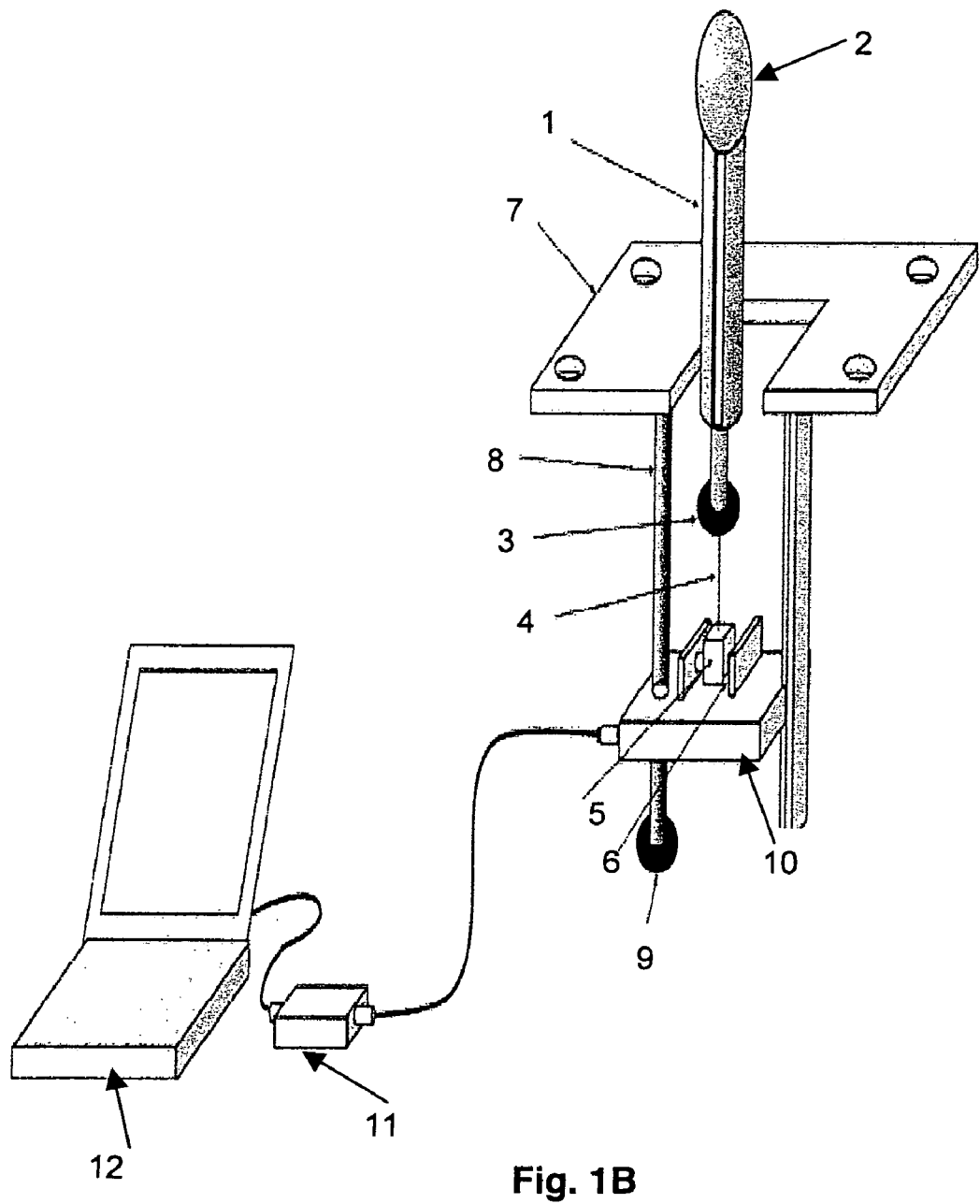
FIG. 1B illustrates different components of the pelvic floor function diagnostic and therapeutic station.

FIG. 1A, shows a model of the instant pelvic floor function diagnostic and therapeutic station. FIG. 1B, shows the different parts of the station. The station includes a catheter holder 1 which has a ball 2 at one end and a holder adjusting knob 3 at the other end. The holder adjusting knob 3 is used to increase or decrease the diameter of the catheter holder 1. This enables increasing the length of the puborectalis muscle when the catheter holder is placed in the rectum of a subject. The catheter holder 1 is further connected at the knob end via a force transfer rod 4 to a vertical force transducer 5, which is placed within a transducer holder 6. The vertical force transducer exerts varying pressure on the catheter holder and ball, which allows increasing and decreasing the resistance against which the pelvic floor muscle may contract. The latter allows measurement of the length tension relationship for that part of the pelvic floor muscle that is responsible for the craniocaudal movements (elevator function).

The catheter holder 1 and the force transducer system are supported by a support 7, which also serves to position the subject for diagnosis or therapeutic use of the pelvic floor function diagnostic and therapeutic station. The support 7 has a position adjusting level 8 and a position adjusting knob 9 for adjusting the position of the subject. The signals recorded by the plug are connected via an anchoring device 10 to a preamplifier/A-D converter 11, which in turn is connected to a computer and software system 12. The preamplifier 11 serves to amplify the signals from the plug and convert it to computer readable signals. The computer and software system 12 evaluates the measurements and based on these values can predict if the subject has normal or defective pelvic floor muscle function. The computer and software program 12 can also use the measurements to provide biofeedback therapy to a subject in need of such therapy using different types of exercises.

Figure 2:
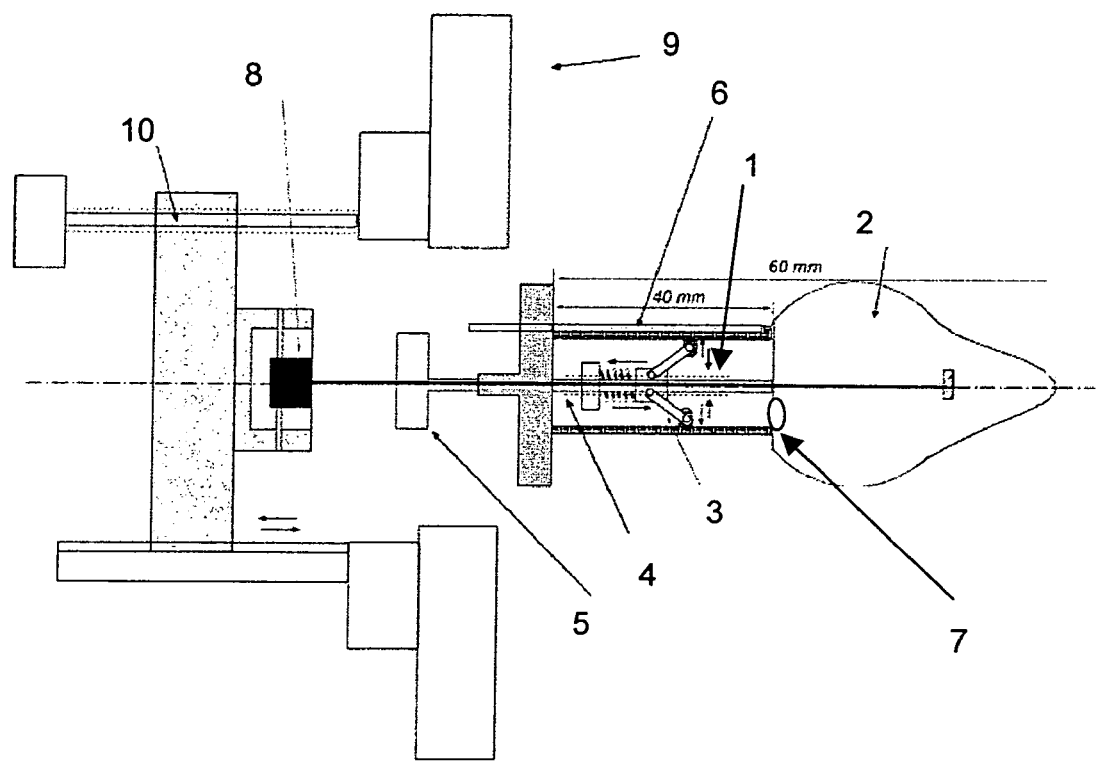
FIG. 2 illustrates the force/pressure module of the pelvic floor function diagnostic and therapeutic station.

FIG. 2 shows the force/pressure module of the vaginal/anorectal plug. The plug includes a catheter holder 1. Preferably the length of the catheter holder 1 is 80 mm. The catheter holder 1 has a ball 2 at one end and preferably the total length of the catheter holder 1 and the ball 2 is 80-100 mm. The diameter of the catheter holder 1 can be increased or decreased via the holder adjusting levels 3, the holder adjusting shaft 4 and the holder adjusting knob 5. The catheter holder has a manometery catheter (or any other pressure or force measuring system) for measuring the pressure exerted on the plug by the subject as a result of constriction function. The ball 2 has a strain gauge sensor 7 (located on the base of the catheter holder) to measure the pressure or vertical force exerted by the pelvic muscle in response to the vertical force from 8. The plug is held in place by a support 9, which as discussed supports position of the subject for diagnostic and therapeutic uses of the instant invention. The position of the support can be adjusted and the position adjusting level 10 is used to position the subject and the plug to enable either diagnosis or therapy using the instant invention.

Figure 3:
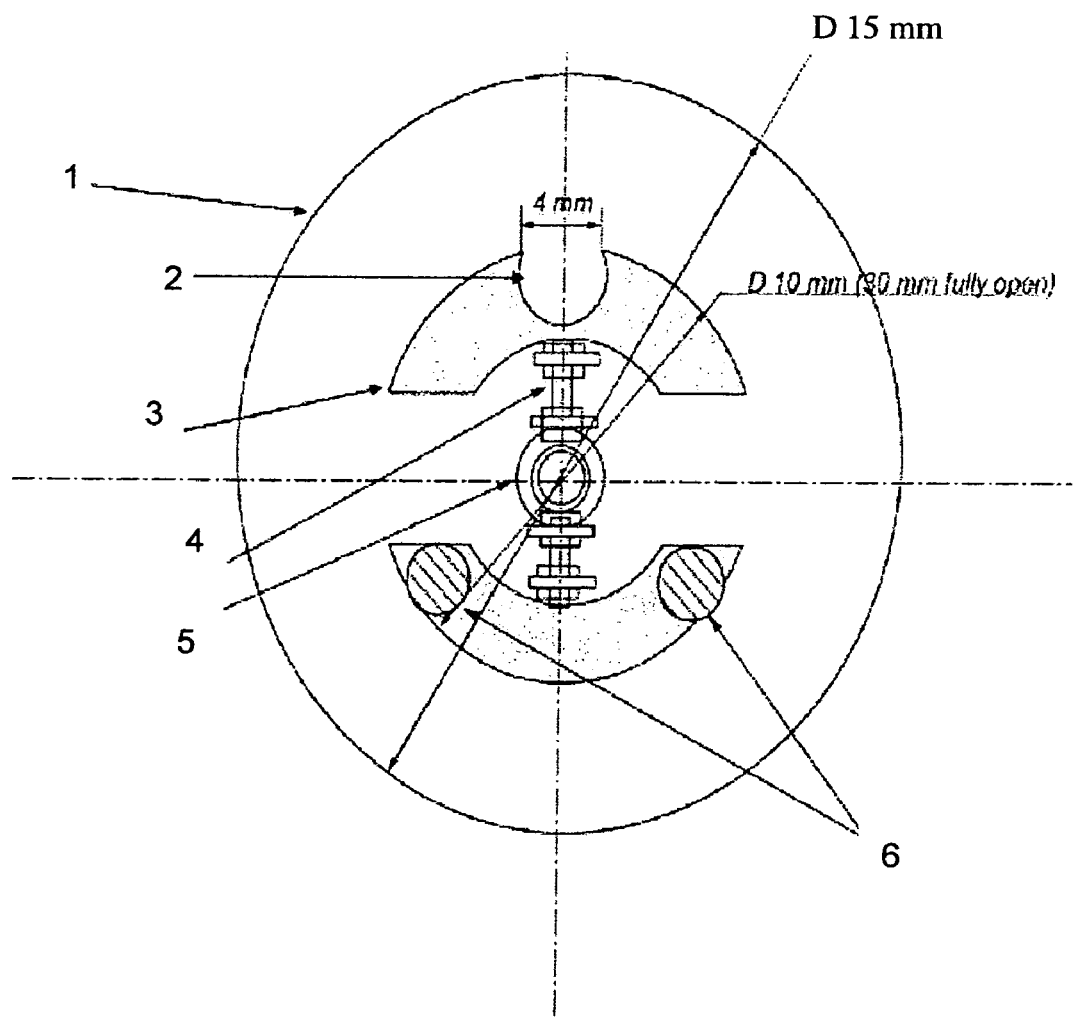
FIG. 3 shows the catheter holder that can be used in the pelvic floor function diagnostic and therapeutic station.

FIG. 3 shows a cross-sectional view of the catheter holder. The ball I of the vaginal/ano-rectal plug preferably has a diameter of 15 mm. The manometery catheter or sleeve sensor 2, which is placed in the catheter holder is preferably 3-4 mm wide. The diameter of the catheter holder can be varied and this variation is preferably from 10-40 mm. 3 shows the elements in the catheter holder that expands. This expansion is mediated by the holder adjusting level 4 and the holder adjusting shaft 5. The catheter holder has electrodes 6 for measuring the EMG activity of the pelvic floor muscles. The electrodes 6 may also be used for electric stimulation of the pelvic floor muscles for therapeutic affect. The electrodes may be made of platinum or other electrical conductive material. Preferably there may be 3 electrodes on the catheter holder.

In general the catheter holder and ball can be any non-compressible material (plastic, resin or electrically non-conductive metal). If an expandable holder and hydrostatic pressure is employed to expand the plug, the material may be silicon, polyvinyl, polyethylene or any other expandable material.

In a preferred embodiment the important components of the pelvic floor diagnostic and therapeutic station are: 1) catheter holder with a sleeve sensor (to measure the constrictor function); 2) vertical force transducer system (to measure the elevator function); and 3) a modular support table or a chair (frame to hold the subject position). The unique feature of the catheter holder is that its diameter can be increased or decreased using a mechanical device, which increases the length of the puborectalis muscle. The catheter holder is placed inside the rectum above the anal high pressure zone or vagina high pressure zone. The subject sits on the chair resting (on both ischial tuberosities) and the vertical tension on the catheter holder and the ball (at the end of the catheter holder) is adjusted to provide baseline tension for measuring the elevator function of the pelvic diaphragm. The baseline tension can be increased using a mechanical system, which allows measurement of elevator function at various baseline tensions. The metal ball, which is present at the tip of the catheter holder anchors against the high pressure zone of the anal canal or the vaginal canal thus allowing monitoring of vertical movement of anal or vaginal canal against different baseline tension exerted by the force transducer.

The following examples are given for the purpose of illustrating various embodiments of the invention and are not meant to limit the present invention in any fashion.

EXAMPLE 1

Side-hole Manometry and Sleeve Sensor Technique to Measure Vaginal Pressure

Elevator function of pelvic diaphragm causes cranial movement of vaginal high pressure zone (HPZ) during contraction but the manometry catheter may not necessarily move with it which can cause motion artifact in the side hole pressure recordings. The second problem with side-hole pressure recording technique is that the vaginal high pressure zone is distributed in a bell shaped manner, i.e., the maximum or peak pressure is located in the center of high pressure zone. It is extremely difficult to keep a side hole at the location of peak pressure, especially when it is moving in the craniocaudal direction. Both of the limitations of side hole pressure recording technique can be overcome by a sleeve sensor, (3). Sleeve sensor is usually 6 cm in length and it records peak pressure along its length, irrespective of the high pressure zone location on the sleeve. The problem with sleeve sensor however is that depending upon the direction and speed of the high pressure zone movement on the sleeve, and the rate of fluid flow in the sleeve sensor, a motion artifact is introduced in the pressure recording (5). This problem is overcome by using a reverse perfuse sleeve sensor in the instant device.

Figure 4A:
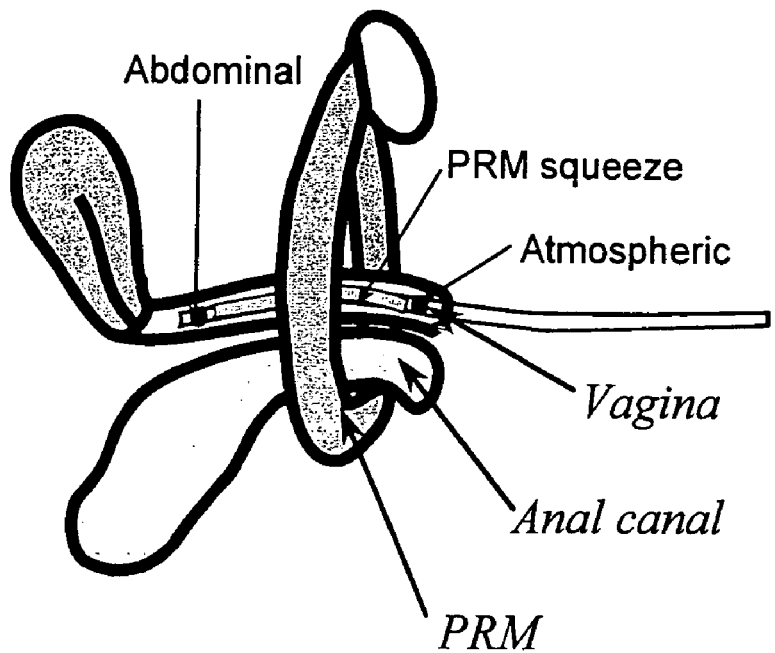
FIG. 4A illustrates measurement of vaginal pressure using a reverse perfuse sleeve sensor. The side hole located a the distal end of the sleeve sensor records abdominal pressure, the sleeve records the puborectalis muscle (PRM) pressure and the side hole at the proximal end of the sleeve records the atmospheric pressure.
Figure 4B:
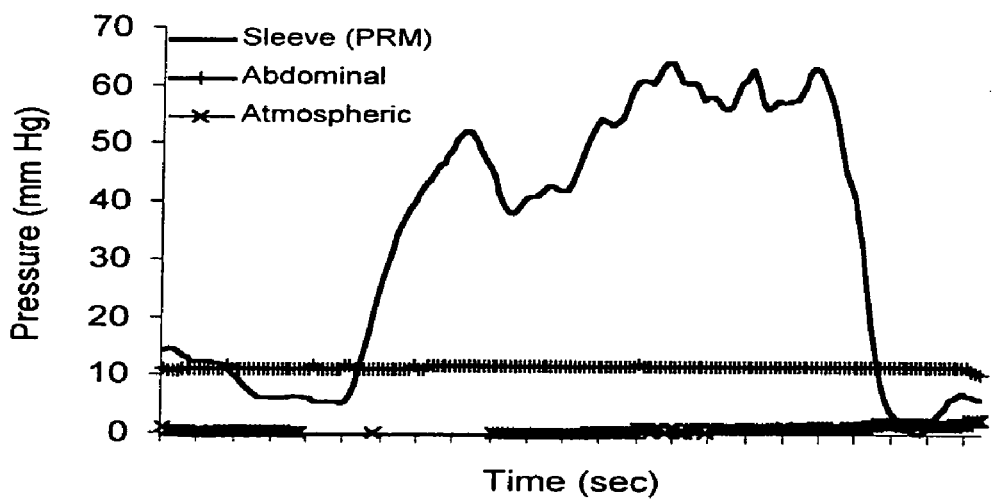
FIG. 4B shows the pressure recordings obtained using the sleeve sensor.

A manometry catheter with side holes located at the proximal and distal ends of a 6 cm long reverse perfuse sleeve sensor is positioned in the vagina using the instant device. The side hole located at the distal end of the sleeve sensor records abdominal pressure, the sleeve records the puborectalis (PRM) pressure and the side hole at the proximal end of the sleeve records the atmospheric pressure. The sensing surface of the sleeve sensor faces the pubic bone because the higher vaginal pressures are directed in the anterior direction or alternatively it may posterior if future observations prove that the posterior pressures are more reproducible. Recordings are performed in the resting state (subject is asked to relax) and then during the sustained squeeze of the pelvic diaphragm muscle. Measurements are repeated to test reproducibility. FIGS. 4A-B illustrates how such measurements are made with a manometry catheter that can be used in the instant device.

EXAMPLE 2

Vaginal Probe Size and Vaginal Pressure Measurement

Figure 5:
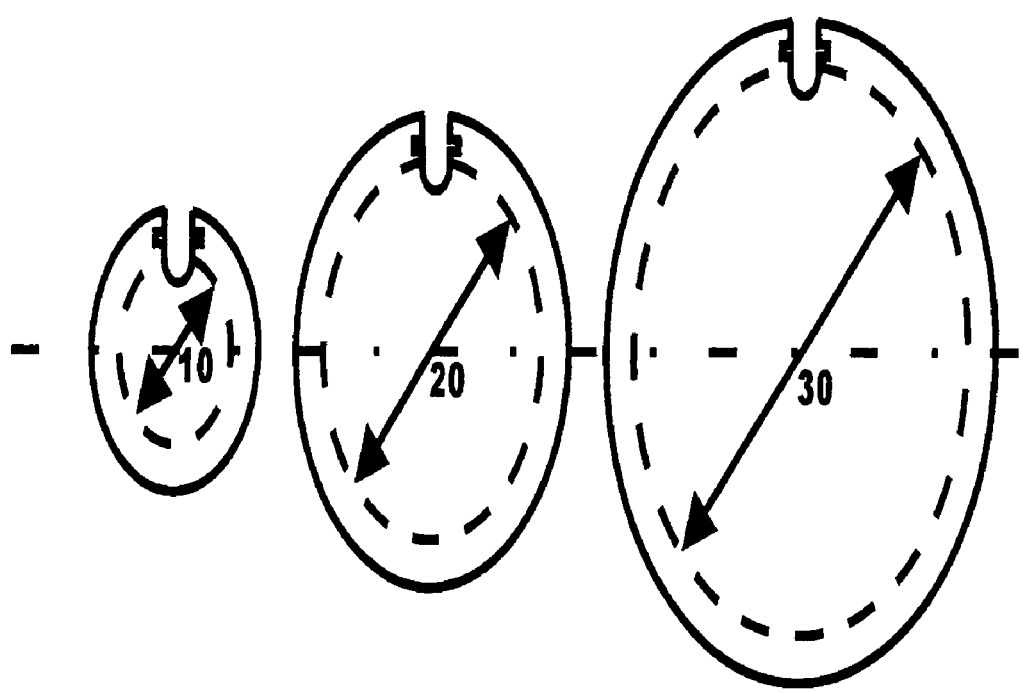
FIG. 5 shows catheter holders of varying diameters that can be used in the instant device.

FIG. 5 illustrates an example of a catheter holder to hold the sleeve sensor used in the instant device. A standard size sleeve sensor can be placed inside the holder and the two (holder+sleeve sensor) are placed inside the vagina. Pressure sensor surface of sleeve sensor faces anterior direction (towards the pubic bone) if one wants to record the anterior vaginal pressure. Holders of different sizes are designed such that irrespective of the size of the holder, a standard 4 mm sleeve catheter fits into the holder. By using different size holders, one can increase the length of the puborectalis muscle and at the same time record pressure at rest and during pelvic floor muscle squeeze.

The following references are cited herein:
1. Constantinou, et al. Pressure components in the Female Urethra: Female Incontinence. New York, N.Y.: Allan R Liss Inc. 113-120 (1981).
2. Sapsford, et al. Arch. Phys. Med. Rehabil. 82:1081-1088 (2001).
3. Kegel A. Am J Obstet Gynecol. 56(2): 238-248 (1948).
4. Dent J. Gastroenterology. 71:263-67 (1976).
5. Sivri B. et al. Gastroenterology. 101:962-9 (1990).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A vaginal/ano-rectal plug sensor and station comprising:
   (a) a means to measure the constrictor function of pelvic floor muscle and its length tension characteristics;
   (b) a means to measure the elevator function of pelvic floor muscle and its length tension characteristics, wherein said constrictor function and said elevator function of said pelvic floor muscle can be measured simultaneously; and
   (c) a modular support table or a chair to hold a subject position.

2. The vaginal/ano-rectal plug sensor and station of claim 1, wherein said modular support table or a chair comprises an anchoring device to which an outer end of said plug is connected.

3. The vaginal/ano-rectal plug sensor and station of claim 2, wherein said anchoring device enables connection of said plug to a computer and software system for making measurements based on the signals detected by said plug and wherein said measurements are processed by said system to provide biofeedback therapy to a subject in need of such therapy.

4. The vaginal/ano-rectal plug sensor and station of claim 1, wherein said means to measure said constrictor function comprises an expandable catheter holder, and said means to measure said elevator function comprises a force transducer.

5. The catheter holder of claim 4, wherein said holder has a manometer and sleeve sensor or an equivalent pressure measurement system.

6. The catheter holder of claim 5, wherein said sleeve sensor is a reverse perfuse sleeve sensor.

7. The catheter holder of claim 4, wherein the diameter of said holder is increased or decreased using a mechanical device.

8. The catheter holder of claim 7, wherein said mechanical device comprises a position adjusting level, a position adjusting shaft and a position adjusting knob.

9. The catheter holder of claim 4, wherein the diameter of said holder varies from about 10 to about 40 mm.

10. The catheter holder of claim 4, wherein the length of the catheter holder is about 80 mm.

11. The catheter holder of claim 4, wherein said holder has surface electrodes.

12. The catheter holder of claim 11, wherein said electrodes can measure either the electromyographic activity of the pelvic floor muscles or can provide therapeutic stimuli to said muscles.

13. The catheter holder of claim 11, wherein said electrodes are made of platinum or other electrically conductive material.

14. The catheter holder of claim 4, wherein said holder has a ball at one end and is connected to said force transducer at the other end via a force transducer rod.

15. The catheter holder of claim 14, wherein said ball has a diameter of about 15-20 mm.

16. The catheter holder of claim 14, wherein said force transducer transmits varying vertical tension to said holder and said ball.

17. The ball of claim 14, wherein said ball has a pressure sensor.

18. The ball of claim 17, wherein said sensor is a strain gauge sensor.

19. The catheter holder of claim 14, wherein said force transducer is contained in a transducer holder.

20. The catheter holder of claim 14, wherein the total length of the catheter holder and ball is about 60-100 mm.

21. A pelvic floor diagnostic and therapeutic station comprising:
   (a) a catheter holder with a sleeve sensor or an equivalent pressure measurement system to measure the constrictor function of pelvic floor muscles and its length tension characteristics;
   (b) a vertical force transducer system to measure the elevator function of said pelvic floor muscles and its length tension characteristics, wherein said constrictor function and said elevator function of pelvic floor muscle can be measured simultaneously;
(c) a modular support table or a chair to hold the subject position; and
(d) a computer and software system to receive and process said measurements from (a) and (b).

* * * * *